United States Patent [19]

Ingram et al.

[11] Patent Number: 5,535,745
[45] Date of Patent: Jul. 16, 1996

[54] AUXILIARY BODY FOR GUIDING A STYLET INTO THE STYLET CHANNEL OF AN IMPLANTABLE MEDICAL ELECTRODE

[75] Inventors: Roy Ingram, Hitchin, Great Britain; Per Nyman, Djursholm, Sweden

[73] Assignee: Pacesetter AB, Solna, Sweden

[21] Appl. No.: 377,261

[22] Filed: Jan. 24, 1995

[30] Foreign Application Priority Data

Jan. 27, 1994 [SE] Sweden .................................. 9400245

[51] Int. Cl.⁶ .................................................. A61M 25/09
[52] U.S. Cl. ............................................ 128/642; 128/772
[58] Field of Search ................................ 128/772, 639, 128/642, 899, 897; 607/120, 116, 1

[56] References Cited

U.S. PATENT DOCUMENTS

| | | |
|---|---|---|
| 4,243,050 | 1/1981 | Littelford . |
| 4,732,163 | 3/1988 | Bonello et al. . |
| 4,800,890 | 1/1989 | Cramer . |
| 5,125,416 | 6/1992 | Phillips ................................... 128/772 |
| 5,186,179 | 2/1993 | MacEachern . |
| 5,191,888 | 3/1993 | Palmer et al. ............................ 128/772 |
| 5,333,620 | 8/1994 | Moutafis et al. ........................ 128/772 |
| 5,376,109 | 12/1994 | Lindegren et al. . |

*Primary Examiner*—William E. Kamm
*Assistant Examiner*—Kennedy J. Schaetzle
*Attorney, Agent, or Firm*—Hill, Steadman & Simpson

[57] ABSTRACT

An auxiliary body, for guiding a stylet into the stylet channel of an electrode cable in a medical electrode device whose proximal end is provided with a connector pin, has a first end provided with a cylindrical channel so the auxiliary body can be pushed onto the connector pin, a second end of the auxiliary body being provided with a cavity whose orifice is larger than the channel's opening. The cavity is connected to the channel and continuously narrows in such a way that the diameter of the channel end of the cavity is larger than the external diameter of the stylet and equal to or less than the diameter of the stylet channel. For drying off and/or lubricating the stylet in a safe and simple manner without any additional, disruptive step in the implantation procedure, a carrier which contains one or both of drying or lubricating agent is disposed in the cavity and/or in the channel of the auxiliary body so as to cause the agent contained in the carrier to interact with the stylet as the stylet is inserted through the auxiliary body.

12 Claims, 1 Drawing Sheet

AUXILIARY BODY FOR GUIDING A STYLET INTO THE STYLET CHANNEL OF AN IMPLANTABLE MEDICAL ELECTRODE

BACKGROUND OF THE INVENTION

1. Field of the Invention

The present invention relates to an auxiliary body for guiding a stylet into the stylet channel of a medical electrode cable to assist in implantation of the cable.

2. Description of the Prior Art

It is well known for a physician, in implanting an intracardiac or intravascular electrode device in a patient, to employ an auxiliary body in order to facilitate insertion of the relatively long, thin stylet into stylet channel of the electrode cable from the proximal end of the electrode cable. Typically the electrode device has proximal end provided with a connector pin, and one end of the auxiliary body is provided with a cylindrical channel so the auxiliary body can be pushed onto the connector pin, and the other end of the auxiliary body is provided with a cavity whose orifice is larger than the channel's opening. The cavity is connected to the channel and continuously narrows in such a way that the diameter of the channel end of the cavity is larger than the external diameter of the stylet and is equal to or less than the diameter of the stylet channel. At this point in the procedure, the physician has already made an opening in a vein for the cable and even prepared implantation of the pacemaker. As a result of these preparations, the physician's rubber gloves are bloody, at least in part. Thus when the stylet is inserted, the stylet could easily become soiled with blood from the gloves. This means that blood could get into the stylet channel, soil the conductor helix and dry there with a glue-like effect, possibly making it necessary to jerk the stylet to remove it from the stylet channel. This could, in turn, cause the part of the electrode cable installed in a vein or the heart to be jerked out of the desired position. To eliminate this problem, the physician, or an assistant, can dry off the stylet with a dry or wet cloth, but this introduces an additional, possibly disruptive step in the implantation procedure. Wiping off the stylet with a cloth, possibly soaked in sterile water, removes any blood and simultaneously gives the stylet a relatively slippery surface which could make insertion of the stylet into the stylet channel easier, however, this lubricating effect is of brief duration.

SUMMARY OF THE INVENTION

An object of the present invention is to provide an auxiliary body of the type described in the introduction above with which a stylet can be dried off and/or lubricated in a safe and simple manner, without any additional, disruptive step during implantation.

The above object is achieved in accordance with the principles of the present invention in an auxiliary body wherein auxiliary body's introductory cavity and/or channel is/are provided with a stylet drying and/or lubricating means. This structure ensures that the auxiliary body is always free from blood before it is inserted into the stylet channel and also prevents the stylet from getting stuck in the stylet channel. In addition, lubrication of the stylet in this simple manner make it easier for the physician to introduce the stylet into the stylet channel.

According to one version of the invention, the drying and/or lubricating means consist of a felt pad. In this way, the means is concentrated to in single unit arranged in the auxiliary body.

Preferably, the felt pad contains alcohol to remove blood from the stylet.

The felt pad can additionally or alternatively contain cottonseed oil which has a lubricating effect on the stylet.

The drying and/or lubricating means can be enveloped in a protective membrane, perforatable by the stylet, to prevent the means from drying out.

In another version of the invention, the drying and/or lubricating means can be detachable. This enables the physician to remove one such means and replace it with another.

DESCRIPTION OF THE PREFERRED EMBODIMENTS

Figure 1:
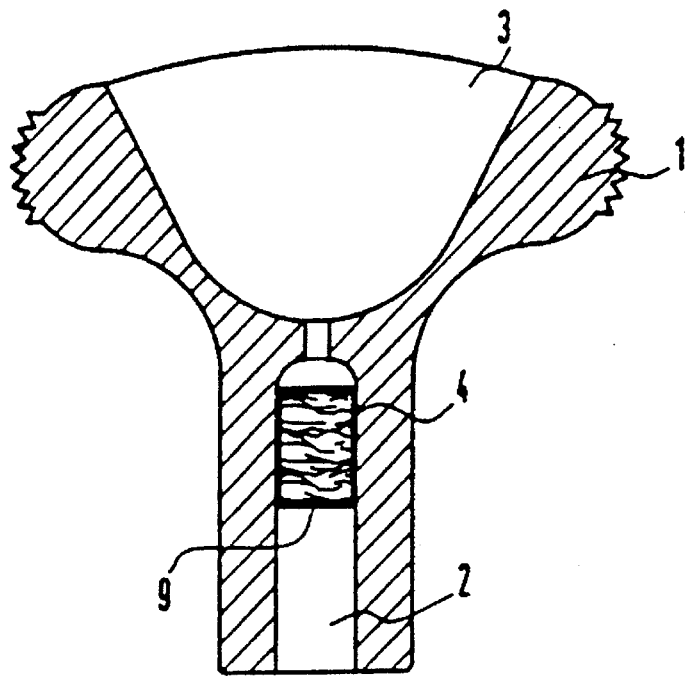
FIG. 1 shows a longitudinal cross-section through an auxiliary body according to the invention.
Figure 2:
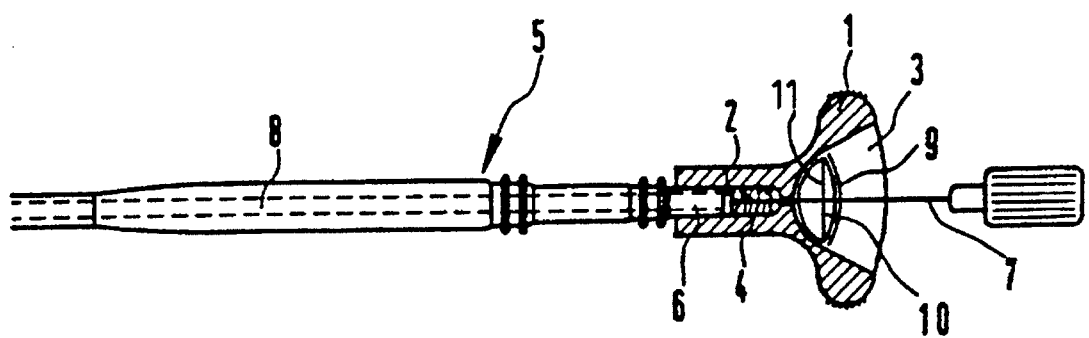
FIG. 2 is a side view of the proximal end of a further embodiment of an electrode device with an auxiliary body mounted thereon.

FIG. I shows an auxiliary body 1 for guiding a stylet into an electrode cable's control channel in an electrode device of the type depicted and described in FIG. 2. One end of the auxiliary body 1 has a cylindrical channel 2, and the other end is provided with an introductory cavity 3, whose opening is larger than the channel 2. The cavity 3 is connected to the channel 2 and continuously narrows in such a way that the diameter of the channel 2 end of the cavity 3 is larger than the diameter of the stylet inserted into the stylet channel, and is equal to or less than the diameter of the stylet channel. As a result of this structure for the auxiliary body 1, a stylet can be inserted into the stylet channel in a very simple manner. A felt pad 4 containing a drying agent, such as alcohol, or a lubricating agent, such as cottonseed oil, is arranged in the channel 2. The felt pad 4 is advantageously enveloped in a protective membrane 9, perforatable by the stylet, to prevent the leakage agent contained therein. The felt pad 4 can alternatively be provided with one layer of alcohol and another layer of cottonseed oil, the layers being separated by a detachable protective membrane. The felt pad 4 is detachable and therefore replaceable.

As shown in FIG. 2 the auxiliary body 1, as a result of its cylindrical channel 2, can be pushed onto the connector pin 6 of the electrode device 5. The felt pad 4 is thereby affixed in the channel 2 by the connector pin 6. The stylet 7 can then be introduced into the stylet channel 8 when the distal end of the stylet is inserted into the cavity 3 in the auxiliary body I and the stylet 7 is pushed into the channel 2 through the felt pad 4. When the stylet 7 reaches the stylet channel 8, the stylet 7 has been cleaned and possibly lubricated.

The pad can alternatively be devised to fit inside the cavity 3 in the auxiliary body 1. The dot-dash lines in the cavity 3 in FIG. 2 indicate the shape and position of such a pad, designated in this example with the reference number 10. One such pad 10 can replace the felt pad 4 arranged in the cylindrical channel 2 in the auxiliary body. The pad 10, which is enveloped in a protective membrane 9, can advantageously contain a gel for softening and drying off any blood on the stylet 7. With the aid of the gel, the stylet 7 can, when inserted into the cavity 3, be easily straightened therein and then introduced into the stylet channel 8 in the ordinary way.

The pad 10 can also be used in combination with the felt pad 4. In this combination, the pad 10 can suitably contain a softening and drying agent in the form of a gel, separated by a membrane 11 and the felt pad 4 can contain a lubricating agent. Alternatively, the pad 10 can contain a softening agent, the felt pad 4 then performing the function of drying off the stylet 7.

The cavity 3 and the channel 2 thus form a stylet guiding path, and the pad 4 and/or the pad 10 can be disposed anywhere along this path.

With the use of the felt pad 4 or the combination of the felt pad 4 plus the gel pad 10, which can contain a drying and/or lubricating agent, the stylet 7 can be simply and safely cleaned of blood and possibly lubricated before the stylet 7 is inserted into the stylet channel 8 of the electrode device 5 during an electrode implantation.

Although modifications and changes may be suggested by those skilled in the art, it is the intention of the inventors to embody within the patent warranted hereon all changes and modifications as reasonably and properly come within the scope of their contribution to the art.

We claim as our invention:

1. An auxiliary body for use with a stylet and a medical electrode device having a proximal end provided with a connector pin and having a stylet channel, for guiding said stylet into said stylet channel via said proximal end, said auxiliary body comprising:

a first end having a cylindrical channel therein insertable over said connector pin;

a second end having an introductory cavity therein having an orifice larger than a diameter of said cylindrical channel, said introductory cavity being connected to said cylindrical channel and continuously narrowing so that a diameter of an end of said introductory cavity adjacent said cylindrical channel is larger than an external diameter of said stylet and equal to or less than a diameter of said stylet channel, said introductory cavity and said cylindrical channel forming a stylet guiding path in said auxiliary body; and means disposed in said stylet guiding path in said auxiliary body for carrying at least one agent selected from the group consisting of drying agents and lubricating agents for releasing said agent onto said stylet as said stylet is advanced through said stylet guiding path.

2. An auxiliary body as claimed in claim 1 wherein said means for carrying said agent is disposed in said introductory cavity.

3. An auxiliary body as claimed in claim 1 wherein said means for carrying said agent is disposed in said cylindrical channel.

4. An auxiliary body as claimed in claim 1 wherein said means for carrying said agent is disposed in both said introductory cavity and in said cylindrical channel.

5. An auxiliary body as claimed in claim 1 wherein said means for carrying said agent comprises a felt pad.

6. An auxiliary body as claimed in claim 1 wherein said means for carrying said agent comprises a protective outer envelope formed by a membrane perforatable by said stylet.

7. An auxiliary body as claimed in claim 1 wherein said means for carrying said agent is removably disposed in said stylet guiding path.

8. An auxiliary body as claimed in claim 1 wherein said means for carrying an agent carries alcohol as a drying agent.

9. An auxiliary body as claimed in claim 1 wherein said means for carrying an agent carries cottonseed oil as a lubricating agent.

10. An auxiliary body for use with a stylet and a medical electrode device having a proximal end provided with a connector pin and having a stylet channel, for guiding said stylet into said stylet channel via said proximal end, said auxiliary body comprising:

a first end having a cylindrical channel therein insertable over said connector pin;

a second end having an introductory cavity therein having an orifice larger than a diameter of said cylindrical channel, said introductory cavity being connected to said cylindrical channel and continuously narrowing so that a diameter of an end of said introductory cavity adjacent said cylindrical channel is larger than an external diameter of said stylet and equal to or less than a diameter of said stylet channel, said introductory cavity and said cylindrical channel forming a stylet guiding path in said auxiliary body; and first carrier means for carrying a first agent for interacting with said stylet as said stylet is inserted through said auxiliary body, said first carrier means being disposed in said introductory cavity;

second carrier means for carrying a second agent for interacting with said stylet as said stylet is inserted through said auxiliary body, said second carrier means being disposed in said cylindrical channel; and said first agent being one agent selected from the group consisting of a lubricating agent and a drying agent, and said second agent comprising the other agent in said group.

11. An auxiliary body for use with a stylet and a medical electrode device having a proximal end provided with a connector pin and having a stylet channel, for guiding said stylet into said stylet channel via said proximal end, said auxiliary body comprising:

a first end having a cylindrical channel therein insertable over said connector pin;

a second end having an introductory cavity therein having an orifice larger than a diameter of said cylindrical channel, said introductory cavity being connected to said cylindrical channel and continuously narrowing so that a diameter of an end of said introductory cavity adjacent said cylindrical channel is larger than an external diameter of said stylet and equal to or less than a diameter of said stylet channel, said introductory cavity and said cylindrical channel forming a stylet guiding path in said auxiliary body; and carrier means disposed in said cylindrical channel for carrying a lubricating agent and a drying agent separated from each other, for interacting with said stylet as said stylet is inserted through said auxiliary body.

12. An auxiliary body as claimed in claim 11 wherein said carrier means comprises a felt pad.

* * * * *